United States Patent [19]

Napier

[11] 4,046,774
[45] Sept. 6, 1977

[54] PROCESS FOR N-PHOSPHORYLATION OF HETEROCYCLIC AMINES

[75] Inventor: Roger P. Napier, Califon, N.J.

[73] Assignee: Mobil Oil Corporation, New York, N.Y.

[21] Appl. No.: 649,393

[22] Filed: Jan. 15, 1976

[51] Int. Cl.$^2$ .......................................... C07D 209/86
[52] U.S. Cl. .............................. 260/315; 260/319.1; 260/326.12 R; 260/326.13; 260/326.16; 260/326.2; 260/326.5 R; 260/326.61
[58] Field of Search ............... 260/315, 319.1, 326.61, 260/313.1, 984, 326.2, 326.5 R, 326.12, 326.16

[56] References Cited
PUBLICATIONS

Kosolapoff, "Organophosphorus Compounds", (1950) pp. 294–295.

Primary Examiner—Henry R. Jiles
Assistant Examiner—R. W. Ramsuer
Attorney, Agent, or Firm—Charles A. Huggett; Ronald J. Cier

[57] ABSTRACT

A process for N-phosphorylating heterocyclic amines, e.g., pyrrole, comprising treating the amine with a complex formed by a mixture of bromotrichloromethane and a trialkyl phosphite.

5 Claims, No Drawings

PROCESS FOR N-PHOSPHORYLATION OF HETEROCYCLIC AMINES

BACKGROUND OF THE INVENTION

1. Field of the Invention

This invention relates to a method of N-phosphorylating acidic heterocyclic amines such as pyrrole and indole.

2. Description of the Prior Art

Greenly et al. in J. Org. Chem., 29 1009 (1964) described a method os phosphorylating pyrrole to produce N-(dimethylphosphonyl) pyrrole in which the potassium salt of pyrrole is reacted with O,O-dimethylphosphorochloridate.

U.S. Pat. No. 3,816,452 describes a method wherein the potassium salt of pyrrole is reacted with dialkyl phosphorochloridite to form an intermediate which is then treated with sulfur to yield a N-(dialkylthiophosphonyl) pyrrole or with an oxygen oxidant to yield N-(dialkyloxyphosphonyl) pyrrole. The products produced from these reactions are disclosed as being useful as flame retardants.

SUMMARY OF THE INVENTION

In accordance with this invention a process is provided whereby selected phosphoramides are readily produced in good yield. Thus a one-step process is provided for the N-phosphorylation of heterocyclic amines comprising treating said amine with an admixture of bromotrichloromethane and a trialkyl phosphite.

This process generally relates to acidic amines such as pyrrole and indole, that is compounds of the general formula:

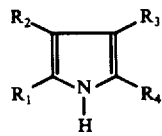

where $R_1$ through $R_4$ are selected from the group consisting of H, $C_1$–$C_{25}$ alkyl, phenyl, substituted phenyl, thienyl, furanyl, cyano, carbalkoxy, carboxy, nitro, alkylthio, alkoxy, halo, haloalkyl etc.; and where $R_1$ and $R_2$ may be connected so as to form an aromatic ring (indole); and where $R_1$ and $R_2$ and $R_3$ and $R_4$ may be connected to form respective aromatic rings (carbazole). The new aromatic rings can also be substituted in the manner described above. More particularly the process relates to such compounds where $R_1$ through $R_4$ are selected from the group consisting of H, $C_1$–$C_4$ alkyl; and where $R_1$ and $R_2$ may be connected so as to form an aromatic ring.

The general process reaction is as follows:

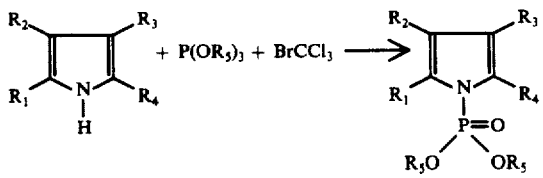

where $R_1$ through $R_4$ are as described above and where $R_5$ is $C_1$ to $C_3$ alkyl.

In the process as disclosed and claimed herein substantially equimolar amounts of the heterocyclic amine and the alkylphosphite are generally used. Suitable alkyl phosphites include those trialkyl phosphites having from 1 to 3 carbon atoms in the alkyl group such as trimethyl-, triethyl, triisopropyl- and tripropylphosphite. Preferred is trimethylphosphite.

The reaction usually comprises the dropwise addition of the trialkylphosphite to a suitable reaction zone which already contains a solution of the heterocyclic amine in the bromotrichloromethane. After about 2–4 hours reaction is completed, the solvent is evaporated and the product obtained is purified by distillation. The reaction procedes well at ambient temperature and pressure, although heat and pressure may be applied if desired.

Among the selected phosphoramides which may be prepared by the method embodied herein are:

N-(Dimethylphosphonyl)pyrrole;
N-(Dimethylphosphonyl)indole;
N-(Dimethylphosphonyl)-3-methylindole;
N-Diisopropylphosphonyl)pyrrole;
N-(Dimethylphosphonyl)-2-methylpyrrole;
N-(Dimethylphosphonyl)-3-ethyl pyrrole;
N-(Diethylphosphonyl)carbazole;
N-(Diethylphosphonyl)-3-phenylindole;
N-(Dimethylphosphonyl)-3-(p-nitrophenyl)pyrrole;
N-(Dimethylphosphonyl)-4-isopropylindole; etc.

The following examples are merely exemplary of the particular reactions they detail and are not to be considered as limitations on this invention.

EXAMPLE I

N-(DIMETHYLPHOSPHONYL) PYRROLE

To a solution of 13.4g of pyrrole (0.20 mole) in 40g (0.20 mole) of bromotrichloroethane 24.8g (0.2 mole) of trimethylphosphite were added dropwise and with stirring so as to maintain resultant exotherm at 40°C. The solution was allowed to cool to room temperature and then stirred for two hours. The solvent was removed with the aid of a rotating evaporator to afford 28.9g of crude product which was distilled to yield 24.1g (68%) of material; b.p. 58°–60° ca. 0.08mm; irvma (film) 3000, 1480, 1310, 1290, 1210, 1050, 855, 800, 780, 740 cm$^{-1}$, nmr $\delta_{TMS}$(CDCl$_3$) 3.66 (d,6), 6.27 (m,2), 6.92 (m, 2) Hz.

Anal. Calcd. for C$_6$H$_{10}$NO$_3$P; C, 41.15; H, 5.76; Found: C, 41.25; H, 5.86.

EXAMPLE II

N-(DIMETHYLPHOSPHONYL) INDOLE

Preparation was in accordance with Example I from 11.7g (0.1 mole) of indole, 25g (0.126 mole) of bromotrichloromethane, and 12.4g (0.1 mole) of trimethylphosphite. Obtained was 21.9g of crude product which was purified by distillation to afford 19.2g (85%) of material (b.p. 105°–114° ca. 0.08mm) which solidified on standing; m.p. 53-54°; vir max (KBr) 3000, 1600, 1510, 1435, 1280, 1155, 1040, 880, 845, 780, 750, 735 cm$^{-1}$; nmr $\delta_{TMS}$(CDCl$_3$), 3.66 (d,6), 6.6 (d of d, 1), 7.2 (m,2), 7.4 (m, 1), 7.65 (m,2) Hz.

Anal. Calcd. for C$_{10}$H$_{12}$NO$_3$P: C, 53.33; H, 5.37; Found: C, 53.20; H, 5.38.

EXAMPLE III

N-(DIMETHYLPHOSPHONYL)-3-METHYLINDOLE

Preparation was in accordance with Example I from 13.1g (0.1 mole) of 3-methylindole, 35g (0.127 mole) of bromotrichloromethane, and 12.4g (0.1 mole) of trimethylphosphite. Obtained were 21.6g of crude product which was purified by distillation to afford 18.3g (76.5%) of the desired material (b.p. 108°-112° ca. 0.05mm) which solidified on standing. Recrystallization from hexane-ether afforded material with m.p. 48°-48.5°: ir$\nu$mac (KBr) 3000, 1600, 1435, 1300, 1270, 1140, 1030, 980, 845, 805, 750 cm$^{-1}$; nmr $\delta_{TMS}$(CDCl$_3$) 2.26 (s,3), 3.70 (d,6), 7.24 (m, 3), 7.50 (m,1), 7.70 (m,1) Hz.

Anal. Calcd. for C$_{11}$H$_{14}$NO$_3$P: C, 55.25, H, 5.85. Found: C, 55.17; H, 5.89.

The examples demonstrate a facile method of preparing selected phosphoramides by the N-phosphorylation of certain acidic heterocyclic amines.

Variations and modifications as understood by one of ordinary skill in the art can be made without departing from the spirit and scope of this invention.

What is claimed is:

1. A process for the N-phosphorylation of heterocyclic acidic amines having the following general formula:

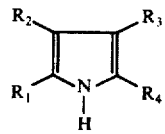

where R$_1$ through R$_4$ are selected from the group consisting of H, C$_1$-C$_{25}$ alkyl, phenyl, carbalkoxyl, carboxy, nitro, alkythio, alkoxy, halo, and haloalkyl; and where R$_1$ and R$_2$ may be connected so as to form an aromatic ring; and where R$_1$ and R$_2$ and R$_3$ and R$_4$ may be connected to form respective aromatic rings comprising treating said amine with a complex formed by a mixture of bromotrichloromethane and a trialkyl phosphite having from 1-3 carbon atoms per alkyl group.

2. A process in accordance with claim 1 wherein the amine and the phosphite are present in substantially equimolar amounts.

3. A process in accordance with claim 1 where R$_1$ through R$_4$ is selected from the group consisting of H, C$_1$-C$_4$ alkyl; and where R$_1$ and R$_2$ may be connected so as to form an aromatic ring.

4. The process in accordance with claim 3 wherein the amine is a pyrrole or an indole and the phosphite is trimethylphosphite.

5. A process in accordance with claim 4 wherein the amine is selected from the group consisting of pyrrole, 2-methyl pyrrole, -3-ethyl pyrrole, carbazole, -3-phenylindole, -3-(p-nitrophenyl)pyrrole and 4-isopropyl-indole.

* * * * *